United States Patent [19]

Schweizer

[11] 4,161,534
[45] Jul. 17, 1979

[54] PROCESS FOR THE PRODUCTION OF NOVEL HYDROXYALKYL DITHIOCARBAMATES

[75] Inventor: Ernst Schweizer, Arlesheim, Switzerland

[73] Assignee: Ciba-Geigy Corporation, Ardsley, N.Y.

[21] Appl. No.: 867,649

[22] Filed: Jan. 6, 1978

[30] Foreign Application Priority Data

Jan. 17, 1977 [CH] Switzerland .......................... 528/77

[51] Int. Cl.$^2$ .................... A61K 31/27; C07C 155/08
[52] U.S. Cl. ................................ 424/300; 260/455 A
[58] Field of Search ..................... 260/455 A; 424/300

[56] References Cited

U.S. PATENT DOCUMENTS 3,342,835  9/1967  Lies ................................. 260/455 A
4,064,265  12/1977  Varsanyi et al. ................ 260/455 A

*Primary Examiner*—Natalie Trousof
*Assistant Examiner*—Robert C. Whittenbaugh
*Attorney, Agent, or Firm*—Theodore O. Groeger

[57] ABSTRACT

Novel hydroxylalkyl dithiocarbamate of the formula

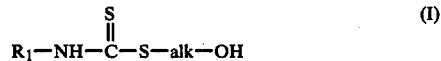

$$R_1-NH-\overset{\overset{S}{\|}}{C}-S-alk-OH \quad (I)$$

wherein $R_1$ represents a phenyloxyphenyl or phenylaminophenyl radical which is unsubstituted or substituted by lower alkyl, halogen, trifluoromethyl, nitro and/or cyano, and alk represents lower alkylene, are useful as anthelmintic agents.

8 Claims, No Drawings

PROCESS FOR THE PRODUCTION OF NOVEL HYDROXYALKYL DITHIOCARBAMATES

The present invention relates to a process for the production of novel hydroxyalkyl dithiocarbamates, in particular those of the formula

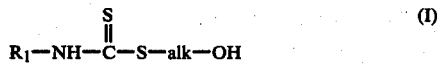     (I)

wherein $R_1$ represents a phenyloxyphenyl or phenylaminophenyl radical which is unsubstituted or substituted by lower alkyl, halogen, trifluoromethyl, nitro and/or cyano, and alk represents lower alkylene, and to these compounds as novel substances, as well as to pharmaceutical preparations which contain said novel substances and the use thereof in the form of such preparations.

A phenyloxyphenyl or phenylaminophenyl radical is in particular a corresponding 4-phenyloxyphenyl or 4-phenylaminophenyl radical. Substituents are preferably present at the phenyloxy or phenylamino group, in particular in the 4-position of this group.

Lower alkyl contains preferably 1 to 4 carbon atoms and is, for example, methyl, ethyl, n-propyl, isopropyl, n-butyl, isobutyl or tert-buryl.

Halogen is preferably halogen having an atomic number up to 35, in particular fluorine or bromine and, most preferably, chlorine.

Lower alkylene represented by alk is preferably unbranched lower alkylene which separates the hydroxyl group from the thio group by at least 2 carbon atoms, and can also be branched lower alkylene, and represents for example ethylene, 1- or 2-methyl-ethylene, 1,3-propylene, 1-, 2- or 3-methyl-1,3-propylene or 1,4-butylene.

The novel compounds have a valuable antiparasitic action, in particular against parasitic helminths. Accordingly, in experimental animals such as mice, pouched mice (*Sarcostomos campestris*), rats, golden hamsters, Mongolian jirds (*Meriones unguiculatus*), dogs, monkeys or fowl, they act, with very good tolerance, against nematoda, such as Ascaridae, for example *Ascaridia galli*, Trichostrongylidae, for example *Nippostrongylus brasiliensis* or *Nematospiroides dubius*, Ancylostomatidae, for example *Necator americanus* and *Ancylostoma ceylanicum*, and Strongylidae, against cestoda, such as *Hymenolepsis nana*, Anoplocephalidae and Taeniidae, and especially against trematoda, such as Fasciola hepatica, and in particular schistosamae, for example *Schistoma mansoni*, *Schistosoma japonicum* and *Schistosoma haematobium*, and in addition against the pathogens of filariasis, for example *Dipetalonema witei* and *Litomosoides carinii*, and of malaria, for example *Plasmodium berghei*. For example, on single administration per os (e.g. with a stomach probe) to golden hamsters which have a 6 to 8-week-old infection of *Schistosoma mansoni*, the compounds of the present invention exhibit an $ED_{50}$ from about 10 to 50 mg/kg and have a curative dosage $ED_{99}$ from about 50 mg/kg. In addition, when used in the treatment of pouched mice (*Sarcostomos campestris*) infected with *Schistosoma haematobium*, in a single oral administration they exhibit an anthelminthic action in the dosage range from about 50 to 200 mg/kg. Furthermore, when administered 1 to 5 times per os in a curative dosage from about 300 mg/kg in the treatment of filariasis in Mongolian jirds infected with *Dipetalonema witei*, the novel compounds prove to be macro- and microfilaricidal. The novel compounds are accordingly useful for the treatment of warm blooded animals infected with parasitic helminths, such as those referred to above, especially in the treatment of schistosomiasis and filariasis.

Preferred compounds are those of the formula I in which $R_1$ represents 4-phenyloxyphenyl or 4-phenylaminophenyl which is unsubstituted or substituted by methyl, chlorine, trifluoromethyl, cyano and/or in particular nitro, such that one substituent is especially in the phenyloxy or phenylamino radical and preferably in the 4-position of this radical, and alk represents the radical of the formula $-(CH_2)_n-$. wherein n is 2, 3 or 4.

The most preferred compounds are those of the formula I, wherein $R_1$ represents 4-(4-nitrophenyloxy)-phenyl or 4-(4-nitrophenylamino)-phenyl, and alk represents the radical of the formula $-(CH_2)_n-$, in which n is 2, 3 or 4, especially 2.

The compounds of the present invention are obtained in a manner known per se. Thus they are obtained, for example, by reacting an isothiocyanate compound of the formula

     (II)

with a mercaptoalkyl compound of the formula

     (III)

The reaction is carried out in the absence, or preferably presence, of a suitable inert, especially polar, solvent or diluent, such as dimethyl formamide or dimethyl sulphoxide, if desired or necessary with cooling or warming (usually in a temperature range between about 0° C. and about 50° C., preferably between about 10° and about 30° C.), and/or in an inert gas atmosphere, such as a nitrogen atmosphere.

The starting materials of the formulae II and III are known or they can be prepared in a manner known per se.

The novel compounds of the formula I can also be obtained by reacting a salt of a dithiocarbamic acid of the formula

     (IV)

with a compound of the formula

     (V)

wherein $Y_1$ and $Y_2$ together represent an adjacent epoxy group, or $Y_1$ represents a reactive esterified hydroxyl group and $Y_2$ represents hydroxyl.

The salt of a compoud of the formula IV is in particular a metal salt, in particular an alkaline earth metal salt and preferably an alkali metal salt, such as a sodium or potassium salt, and also an ammonium salt. A reactive esterified hydroxyl group $Y_1$ is in particular halogen, preferably halogen having an atomic number higher than 9, especially chlorine or bromine and also iodine, furthermore an organic sulphonyloxy group, such as lower alkylsulphonyloxy, for example methylsulphonyloxy, or arylsulphonyloxy, for example 4-methylphenylsulphonyloxy, 4-bromophenylsulphonyloxy or 3-nitrophenylsulphonyloxy.

The reaction is carried out in a manner known per se, for example in the absence or preferably in the presence of a solvent or diluent, such as dimethyl formamide or dimethyl sulphoxide, if necessary with cooling or warming, in a closed vessel and/or in an inert gas atmosphere, for example a nitrogen atmosphere.

The starting materials of the formula IV can be obtained in a manner known per se, for example by treating an aniline compound of the formula

$$R_1-NH_2 \qquad (VI)$$

with carbon disulphide in the presence of aqueous ammonia or with an alkali metal xanthogenate, such as potassium ethylxanthogenate. Like the starting materials specifically referred to, the most important compounds of the formula V are known, and new compounds can be prepared in analogous manner to the known ones.

The novel compounds of the formula I can furthermore be obtained by solvolysing the group $Y_3$ in a dithiocarbamic acid ester compound of the formula

$$\underset{R_1-NH-C-S\text{-alk-}Y_3}{\overset{S}{\|}} \qquad (VII)$$

wherein $Y_3$ represents a group which can be converted by solvolysis into hydroxy.

Radicals $Y_3$ which can be converted by solvolysis into hydroxy are in particular radicals which can be hydrolysed to hydroxy, for example halogen atoms, for example chlorine, bromine or iodine atoms, or acyloxy radicals, such as esterified or amidated carboxyloxy groups, for example oxycarbonyloxy radicals, such as lower alkoxycarbonyloxy radicals, for example tert-butoxycarbonyloxy or ethoxycarbonyloxy, aralkoxycarbonyloxy radicals, such as phenyllower alkoxycarbonyloxy radicals, for example benzyloxycarbonyloxy, halogencarbonyloxy radicals, for example chlorocarbonyloxy, optionally halogenated, such as fluorinated, lower alkanoyloxy radicals, for example formyloxy, acetoxy or trifluoroacetoxy, or benzoyloxy radicals, as well as silyloxy radicals, such as the trimethylsilyloxy radical.

The solvolysis of a group $Y_3$ into hydroxy is preferably effected by hydrolysis, which is preferably carried out in the presence of an acid, for example an aqueous mineral acid, such as sulphuric acid or a hydrohalic acid, or an organic acid, for example a suitable carboxylic acid, such as an α-halogenalkanecarboxylic acid, for example trifluoroacetic or chloroacetic acid, an organic sulphonic acid, for example benzene- or toluenesulphonic acid, or of ion exchangers, or, in particular, in the hydrolysis of halogen $Y_3$, in the presence of a base, for example an alkali hydroxide, such as sodium hydroxide. Oxycarbonyloxy radicals can advantageously be hydrolysed by an acid, for example by a hydrohalic acid. Particularly suitable in this connection is for example hydrolysis with aqueous hydrochloric acid, optionally in admixture with acetic acid. Furthermore, tert-butoxycarbonyloxy for example can be solvolysed into hydroxy under anhydrous conditions by treatment with a suitable acid, such as trifluoroacetic acid.

If necessary, it is possible to add a water-miscible organic solvent, for example a lower alkanol, such as methanol or ethanol, or dioxane, during the solvolysis, and/or to carry out the solvolysis with heating.

The invention also comprises those embodiments of the process in which compounds occurring as intermediates are used as starting materials and the remaining steps are carried out therewith, or the process is discontinued at any stage. Starting materials can also be used in the form of derivatives or formed during the reaction.

The starting materials and reactions conditions used in the above steps are preferably those which result in the compounds described above as particularly preferred being obtained. New starting materials and intermediates as well as processes for the manufacture thereof likewise constitute an object of the invention.

The novel compounds are preferably used in the form of pharmaceutical preparations which are chiefly suitable for oral administration.

The pharmaceutical preparations, which also constitute an object of the present invention, contain from about 10% to about 95% of the active ingredient. Preferred preparations are those for oral administration, such as sugar-coated tablets, tablets or capsules, and also suspensions. The solid preparations contain per dosage unit form from about 0.1 g to about 1.5 g, preferably from about 0.25 g to about 1 g, of active ingredient, whereas liquid preparations contain from about 0.5% to about 15% of active ingredient.

The pharmaceutical preparations are prepared in a manner known per se, for example by conventional mixing, granulating and sugar-coated methods. Pharmaceutical preparations which are suitable for oral administration can be obtained by combining the active ingredient, which, if desired, can be in micronised form, with solid carriers, optionally granulating the mixture thereby obtained, and processing the mixture or granules, if desired and/or optionally after the addition of suitable adjuncts, to tablets or sugar-coated tablet cores.

Suitable carriers are in particular fillers, such as sugar, for example, lactose, saccharose, mannitol or sorbitol, cellulose preparations and/or calcium phosphates, e.g. tricalcium phosphate or calcium hydrogen phosphate, also binders such as starch pastes, for example maize, corn, rice or potato starch paste, gelatin, tragacanth, methyl cellulose, hydroxypropylmethylcellulose, sodium carboxymethylcellulose and/or polyvinylpyrrolidone, and/or, if desired, disintegrators, such as the above starches, also carboxymethyl starch, cross-linked polyvinylpyrrolidone, agar, alginic acid or a salt thereof, such as sodium alginate. Adjuncts are chiefly glidants and lubricants, for example, silicic acid, talc, stearic acid or salts thereof, such as magnesium stearate or calcium stearate, and/or polyethylene glycol. Sugar-coated tablet cores are provided with suitable coatings that can be resistant to gastric juices, using, inter alia, concentrated sugar solutions which may contain gum arabic, talc, polyvinylpyrrolidone, polyethylene glycol and/or titanium dioxide, shellack solutions in suitable organic solvents or solvent mixtures or, for the preparation of coatings resistant to gastric juices, solutions of suitable cellulose preparations, such as acetylcellulose phthalate or hydroxypropylmethylcellulose phthalate. Dyes or pigments can be added to the tablets or sugar-coated tablet cores, for example to identify or indicate different doses of active ingredient.

Further pharmaceutical preparations for oral administration are dry-filled capsules, and also soft sealed capsules made from gelatin and a softener, such as glycerin or sorbitol. The dry-filled capsules can contain the active ingredient in the form of granules, for example in admixture with fillers such as maize starch, binders and/or lubricants, such as talc or magnesium stearate, and optionally stabilisers. In soft capsules, the active ingredient is preferably dissolved or suspended in suitable liquids, for example in fatty oils, paraffin oil or liquid polyethylene glycols, to which stabilisers can also be added.

Suspensions for oral use are in particular aqueous suspensions which contain, for example, stabilisers for increasing the viscosity and retarding sedimentation, such as water-soluble cellulose ethers, for example, carboxymethylcellulose and salts thereof, such as the sodium salt, or methylcellulose, and wetting agents such as sodium lauryl sulphate or dioctyl sodium sulphosuccinate, or nonionic wetting agents, such as polyoxyethylenesorbitan-fatty acid ester or polyethylene glycol/polypropylene glycol copolymers, and to which can be added, if desired or necessary, preservatives, such as 4-hydroxybenzoic acid lower alkyl ester, such as the corresponding methyl, ethyl or n-propyl esters, and/or flavouring and/or sweeting substances.

It is a further object of the present invention to provide a method of treating infections caused by parasitic helminths in warm-blooded animals, which method comprises administering the new compounds of the formula I or salts thereof. In this method, the above pharmaceutical preparations are used in particular for oral administration, such that a daily dose from about 0.25 g to about 1.5 g, preferably from about 0.5 g to about 1.0 g, of the active ingredient is administered to a warm-blooded animal of about 70 kg body weight. In general, a single treatment is sufficient.

The following Examples illustrate the invention, but do not in any way limit the scope thereof.

EXAMPLE 1

47.5 g of 4-(4-nitroanilino)-phenylisothiocyanate and 63 g of 2-mercaptoethanol are stirred in 200 ml of dimethyl formamide for 48 hours at room temperature. With vigorous stirring, the solution is then added dropwise to 5 liters of ice-water. The precipitated N-[4-nitroanilino)-phenyl]-S-(2-hydroxyethyl)-dithiocarbamate is collected by suction filtration, dried, and recrystallised from glacial acetic acid/water. It melts at 74°–76° C. In analogous manner, N-[4-(4-nitrophenoxy)-phenyl]-S-(2-hydroxyethyl)-dithiocarbamate can also be prepared starting from 4-(4-nitrophenoxy)-phenylisothiocyanate.

EXAMPLE 2

0.5 g of N-[4-(4-nitroanilino)-phenyl]-S-(2-acetoxyethyl)-dithiocarbamate is heated for 2 hours in 40 ml of 1 N aqueous ethanolic hydrochloric acid, to give N-[4-(4-nitroanilino)-phenyl]-S-(2-hydroxyethyl)-dithiocarbamate which melts at 74.6° C. after two recrystallisations from glacial acetic acid/water.

The starting material can be prepared by a method analogous to that of Example 1 by reacting 4-(4-nitroanilino)-phenylisothiocyanate with 2-acetoxyethylmercaptan.

EXAMPLE 3

23 q of 4-(4-nitroanilino)-aniline are dissolved, with heating, in 40 ml of toluene and 60 ml of tetrahydrofurane. After cooling to 0°–5° C., ammonia is introduced over the course of 15 minutes. Then 65 ml of carbon disulphide, and afterwards at room temperature 8.8 g of 2-chloroethanol in 20 ml of tetrahydrofurane, are added dropwise. After stirring overnight, the precipitate is collected by suction filtration and washed well with ether. The N-[4-(4-nitroanilino)-phenyl]-S-(2-hydroxythyl)-dithiocarbamate melts at 74°–76° C. after recrystallisation from glacial acetic acid/water and is identical with the product described in Example 1.

EXAMPLE 4

11.5 g of 4-(4-nitroaniline)-aniline are dissolved, with warming, in 20 ml of toluene and 30 ml of tetrahydrofurane. The solution is cooled to 0°–5° C. and then ammonia is introduced, followed by the dropwise addition of 3.3 ml of carbon disulphide. Ethylene oxide is then slowly introduced after 20 minutes. After 6 hours, the reaction mixture is warmed to room temperature and stirred overnight. The N-[4-(4-nitroanilino)-phenyl]-S-(2-hydroxyethyl)-dithiocarbamate is collected by suction filtration, washed with ether and recrystallised from glacial acetic acid/water. Melting point: 74°–76° C.

EXAMPLE 5

6.3 g of 2-mercaptoethanol are added dropwise to a solution of 4.7 g of 4-(4-nitrophenoxy)-phenylisothiocyanate in 20 ml of dimethyl formamide. After stirring for 48 hours at room temperature, the solution is added dropwise, with vigorous stirring, to 250 ml of ice-water. The precipitated N-[4-(4-nitrophenoxy)-phenyl]-S-(2-hydroxyethyl)-dithiocarbamate melts at 128°–130 ° C.

EXAMPLE 6

A solution of 4.7 g of 4-(4-nitroanilino)-phenylisothiocyanate and 8.5 g of 3-mercapto-n-propanol in 40 ml of dimethyl formamide is stirred until the reaction is complete and then added dropwise to 600 ml of ice-water. N-[4-(4-nitroanilino)-phenyl]-S-(3-hydroxy-n-propyl)-dithiocarbamate crystallises and is collected by suction filtration. Melting point: 78°–80° C.

EXAMPLE 7

Tablets containing 0.5 g of N-[4-(4-nitroanilino)-phenyl]-S-(2-hydroxyethyl)-dithiocarbamate can be prepared as follows:

| Composition (for 10,000 tablets) | |
|---|---|
| N-[-4-(4-nitroanilino)-phenyl]-S-(2-hydroxyethyl)-dithiocarbamate | 5000 g |
| corn starch | 790 g |
| stearic acid | 30 g |
| magnesium stearate | 30 g |
| talc | 400 g |
| water | q.s. |

A mixture of the N-[4-(4-nitroanilino)-phenyl]-S-(2-hydroxyethyl)-dithiocarbamate and 500 g of corn starch is made into a paste with about 1300 ml of demineralised water and uniformly moistened with a further 600 g of demineralised water. The mixture is kneaded to a slightly plastic mass, which is forced through a sieve having a mesh size of about 3 mm. The granulate thereby obtained is then dried and sieved. The dry granulate, which is brought to a uniform partical size, is mixed with the magnesium stearate, stearic acid, talc and 290 g of corn starch, and the mixture is compressed to tablets of 0.625 g.

Tablets containing 0.5 g of the respective compound of Example 5 or 6 can be prepared in analogous manner.

What is claimed is:

1. A hydroxyalkyl dithiocarbamate of the formula

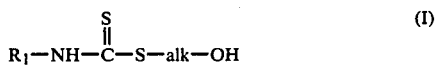

wherein $R_1$ represents a phenyloxyphenyl or phenylaminophenyl radical which is unsubstituted or substituted by lower alkyl, halogen, trifluoromethyl, nitro and/or cyano, and alk represents lower alkylidene or lower alkylene.

2. A compound of the formula I as claimed in claim 1 wherein $R_1$ represents 4-phenyloxyphenyl or 4-phenylaminophenyl which is unsubstituted or substituted by methyl, chlorine, trifluoromethyl, cyano and/or nitro, and alk represents the radical of the formula —$(CH_2)_n$—, wherein n is 1, 2 or 3.

3. A compound of the formula I as claimed in claim 1 wherein $R_1$ represents 4-(4-nitrophenyloxy)-phenyl or 4-(4-nitrophenylamino)-phenyl and alk represents the radical of the formula —$(CH_2)_n$—, wherein n is 1, 2 or 3.

4. A compound as claimed in claim 1 being N-[4-(4-nitrophenyloxy)-phenyl]-S-(2-hydroxyethyl)-dithiocarbamate.

5. A compound as claimed in claim 1 being N-[4-(4-nitroanilino)-phenyl]-S-(2-hydroxyethyl)-dithiocarbamate.

6. A compound as claimed in claim 1 being N-[4-(4-nitroanilino)-phenyl]-S-(3-hydroxy-n-propyl)-dithiocarbamate.

7. A pharmaceutical preparation which contains a compound as claimed in claim 1.

8. Method of treatment of helminthoses characterised in that a compound as claimed in claim 1 is administered to a warm-blooded being.

* * * * *